United States Patent
Capone

(10) Patent No.: US 10,251,581 B2
(45) Date of Patent: Apr. 9, 2019

(54) NASAL AIRFLOW MEASURING DEVICES AND METHODS

(71) Applicant: Randolph B. Capone, Perry Hall, MD (US)

(72) Inventor: Randolph B. Capone, Perry Hall, MD (US)

( * ) Notice: Subject to any disclaimer, the term of this patent is extended or adjusted under 35 U.S.C. 154(b) by 550 days.

(21) Appl. No.: 15/060,253

(22) Filed: Mar. 3, 2016

(65) Prior Publication Data

US 2016/0296138 A1 Oct. 13, 2016

Related U.S. Application Data

(60) Provisional application No. 62/193,423, filed on Jul. 16, 2015, provisional application No. 62/146,614, filed on Apr. 13, 2015.

(51) Int. Cl.
*A61B 5/08* (2006.01)
*A61B 5/087* (2006.01)
*A61B 5/00* (2006.01)

(52) U.S. Cl.
CPC ............ *A61B 5/087* (2013.01); *A61B 5/082* (2013.01); *A61B 5/0873* (2013.01); *A61B 5/6819* (2013.01); *A61B 5/742* (2013.01); *A61B 2562/029* (2013.01)

(58) Field of Classification Search
CPC .................... A61B 2562/029; A61B 5/6819
See application file for complete search history.

(56) References Cited

U.S. PATENT DOCUMENTS

2013/0245483 A1* 9/2013 Eichler ............... A61B 5/082
600/532

OTHER PUBLICATIONS

Viorel Dumitru, et al.,"InN Based Water Condensation Sensors on Glass and Flexible Plastic Substrates"; Sensors, vol. 13, Issue 12, Dec. 6, 2013; www.mdpi.com/journal/sensors.

* cited by examiner

*Primary Examiner* — Puya Agahi
(74) *Attorney, Agent, or Firm* — Grady L. White; Potomac Law Group, PLLC

(57) ABSTRACT

Devices and methods for measuring and quantifying airflow through the adult human nose by detecting and measuring the amount of moisture condensate in contact with a pair of flat surfaces or substrates positioned beneath the patient's nose for a predetermined length of time, usually about three (3) seconds. The device comprises a microprocessor, a memory, an output device and a moisture sensing unit. The moisture sensing unit, comprising twin left and right detectors, produces output signals representative of the amounts of moisture condensate in contact with the left and right detectors, respectively. The microprocessor determines the volume density, current density, or relative humidity density from a series of measurements of the condensation as it propagates and decays during exhalation. The microprocessor stores the results in the memory and transmits the data, as well as calculated nasal condition information, to the output device, preferably a digital display. The device and techniques for using the device are useful in diagnosing nasal obstructions, documenting patient symptoms, and assessing potential responses to therapy.

19 Claims, 10 Drawing Sheets

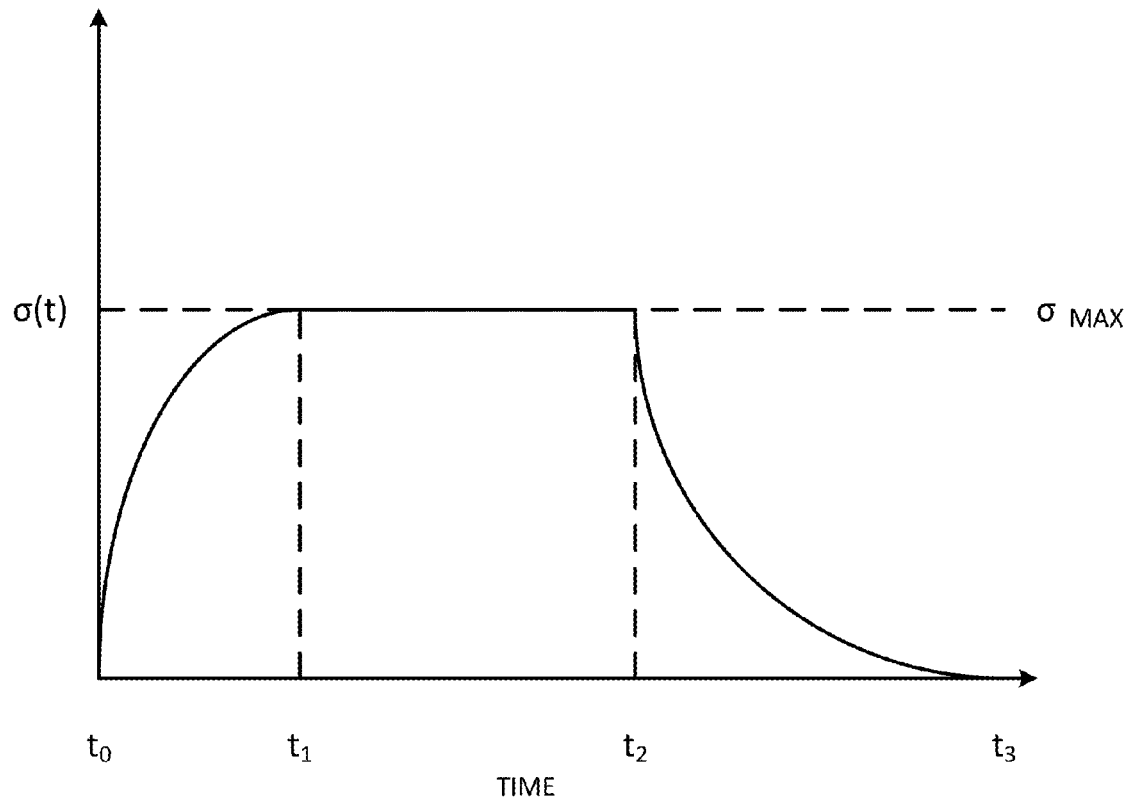

FIG. 2

| $t_0$ | FLOW START ($\sigma$ = 0): PLUME OF CONDENSATION STARTS TO GROW ON GLASS SURFACE |
| $t_0$ TO $t_1$ | SIZE OF CONDENSATION PLUME CONTINUES TO GROW AS THE VOLUME OF EXHALED AIR STRIKING SURFACE INCREASES |
| $t_1$ TO $t_2$ | STEADY STATE (RATE OF CONDENSATION = RATE OF EVAPORATION) |
| $t_2$ | FLOW STOPS (EVAPORATION ONLY) |
| $t_2$ TO $t_3$ | PLUME DECAYS AS CONDENSATE EVAPORATES |
| $t_3$ | EVAPORATION COMPLETE ($\sigma$ = 0) |

| | EXAMPLES OF DIGITAL OUTPUT |
|---|---|
| $\Delta_A$ | CURRENT DROP AS MEASURED FROM A |
| $\Delta_B$ | CURRENT DROP AS MEASURED FROM B |
| $\Delta_A + \Delta_B$ | TOTAL CURRENT DROP FROM THE NOSE |
| $\Delta_A / \Delta_B$ | RATIO OF CURRENT DROPS A & B |

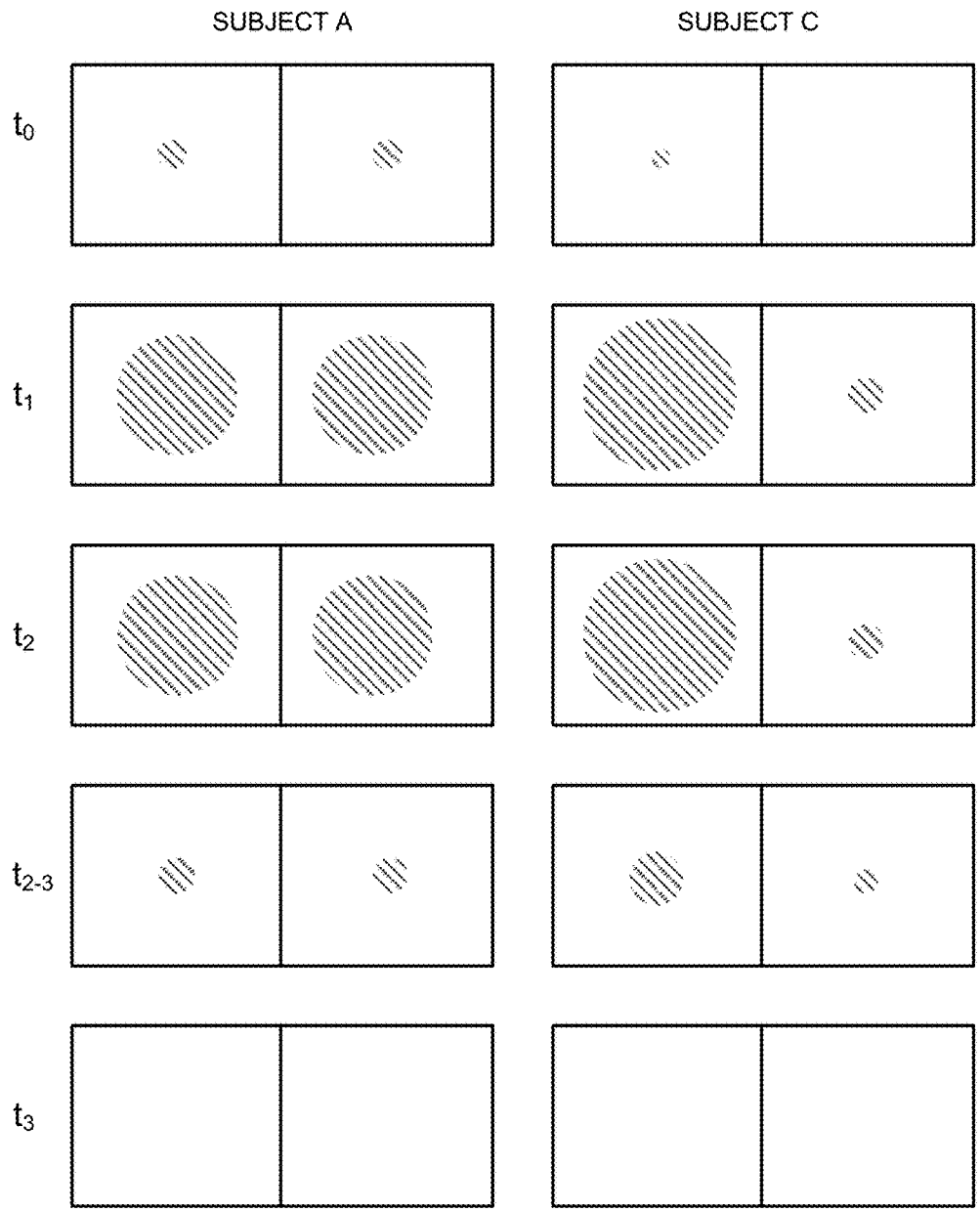

NASAL AIRFLOW MEASURING DEVICES AND METHODS

CROSS-REFERENCE TO RELATED APPLICATIONS

This application is related to and claims priority under 35 U.S.C. § 119 to U.S. provisional patent application No. 62/146,614 filed on Apr. 13, 2015, and to U.S. provisional patent application No. 62/193,423 filed on Jul. 16, 2015, which are both incorporated into this application in their entirety by this reference.

FIELD OF ART

The present invention relates generally to devices and methods for treating nasal conditions, and more particularly to handheld electronic devices, as well as techniques for using such devices, that permit physicians, researchers, and other health care providers to examine, diagnose and treat chronic nasal obstructions (CNO).

BACKGROUND

Chronic nasal obstruction (CNO) is a health disorder with global incidence and morbidity, the diagnosis and management of which is a major health expense. CNO can occur in various forms, including incomplete or complete, unilateral or bilateral, and in various combinations. Billions of dollars are spent annually on pharmaceuticals, allergy testing, allergy immunotherapy, nasal dilators, nasal strips (e.g. Breathe Right® strips) and other over-the-counter nasal aids, physician office visits, and surgical therapy to improve the nasal airway. Despite this, no simple, reliable, quantitative measure of CNO is currently available in the physician office that allows more accurate diagnosis, patient education, or assessments of therapeutic benefit after treatment (outcomes measure). Current methods including acoustic rhinometry and acoustic rhinomanometry have failed in this regard largely due to inaccuracy, lack of reliability, and the requirement for large, bulky instrumentation that is time consuming and virtually impossible to utilize in the clinical setting. Other than physical examination (nose exam, anterior rhinoscopy, nasal endoscopy), there is currently no objective measure of nasal airway obstruction in mainstream healthcare.

Accordingly, there is a need for a diagnostic measuring and method that may be available to medical practitioners or respiratory physiologists, which would provide objective measurements of nasal passage airflow, and do so in a manner that is both reliably accurate and precise while being unobtrusive to the patient. The target users for such devices include otolaryngologists, facial plastic surgeons, allergists, nasal physiologists, internists and family medicine practitioners. Not only would such measurements be useful in diagnosis, but also for measuring and tracking treatment outcomes for a variety of different nasal conditions.

SUMMARY OF EXEMPLARY EMBODIMENTS OF THE INVENTION

The present invention addresses this need by providing devices and methods for assessing airflow through the adult human nose by examining water content of exhaled nasal air. In general, a microprocessor determines the volume density, current density, or relative humidity density from a series of measurements of the plumes of condensate deposited on a surface by exhalation of a patient. The microprocessor also stores the results in a memory and transmits the data, as well as calculated nasal condition information, from the memory to a digital display. In one embodiment, the device for assessing airflow measures the amount of condensate deposited on the moisture-receiving surface using twin indium nitride (InN) condensation sensors. In another embodiment, the device uses twin cameras to measure the amount of condensate optically. In yet another embodiment, the device uses twin relative humidity sensors to assess airflow. It will be understood by those skilled in the art, however, that other types of sensors capable of detecting and measuring condensation plumes on a surface may be used.

More specifically, embodiments of the present invention quantify airflow through a patient's nose using a microprocessor, a memory, an output device and a moisture sensing unit. The moisture sensing unit comprises a left nostril detector and a right nostril detector, wherein each detector is configured to produce output signals representative of the amounts of moisture currently in contact with the left and right detectors, respectively. The practitioner positions the moisture sensing unit near the patient's nose while the patient exhales for a predetermined length of time so that a substantial portion of the air expelled from the left nostril of the patient's nose during the exhalation will strike the left detector and a substantial portion of the air expelled from the right nostril of the patient's nose during the exhalation will strike the right detector. Preferably, the predetermined length of time is three (3) seconds. However, devices and methods of the current invention may be configured to operate for shorter lengths of time (e.g., for two seconds), longer lengths of time (e.g., for five seconds), or any length of time between, depending on the patient's physical anatomy and nasal condition.

During the exhalation for the predetermined length of time, the measuring device repetitively records the output signals produced by the left and right detectors of the moisture sensing unit, thereby generating a plurality of discrete output signals for the left and right nostrils, respectively. The plurality of discrete output signals, which are stored in the memory off the device, represents the changes in output signals produced by each detector in response to changes in the amount of moisture in contact with each detector. The microprocessor calculates a left nostril flow density by summing the discrete output signals in the plurality of discrete output signals for the left nostril. The microprocessor also calculates a right nostril flow density by summing the discrete output signals in the plurality of discrete output signals for the right nostril. The microprocessor then presents the left nostril flow density and the right nostril flow density on the output device, which typically comprises one or more display screens.

Embodiments of the present invention operate on the principle that moisture carried by the outward flow of human exhalation can be measured and quantified. The amount of water lost during respiration has been calculated from the Antoine equation and the ideal gas law, and is dependent upon ambient temperature, relative humidity, and the subject's minute ventilation (Pneumonol Alergol Pol. 2012; 80(4):339-42). Direct measurement of the mass of water that condenses on the surface in response to nasal exhalation can be used to assess the amount of flow from the nose, and from each nostril comparatively. In a normal human subject, this can be roughly approximated as follows:

Volume of air exhaled=tidal volume=7 cc/kg=490 ml assuming a 70 kg subject.

Water content of exhaled air=0.053 g/l, assuming 37° C. at 100% relative humidity.

Mass of water exhaled=0.026 g/exhalation.

Volume of water exhaled per nostril=0.013 cc/exhalation, if nasal passages are equivalent.

When a flat glass surface (e.g. a mirror) is held directly under the nose, orthogonal to the upper lip at the base of the nose, tidal exhalation from the nose in a human subject produces visible condensation on the surface. This condensation pattern is typically described by two discrete circular areas (one per nostril) separated by an area devoid of condensation (hereafter referred to as 'the columellar shadow'). Within several seconds after exhalation stops, the condensation plumes shrink in size and disappear as the condensate evaporates. This observation can be used to assess overall flow from the nose, as well as to judge the difference in airflow between the two nostrils. Because exhalational flow approximates inhalational flow with tidal respiration, this technique can used in the diagnosis of nasal obstruction, to evaluate patient symptoms, and to assess the response to therapy.

The air expelled from human lungs is relatively consistent in water content; however, ambient temperature and relative humidity can change from day to day and from geographic location to location, so ideally any measurements of exhaled water content are carried out in a climate controlled office or stable laboratory environment. By normalizing these variables, meaningful measurement of condensation can be performed and compared. If these variables differ, the condensation and evaporation rates would vary as well. A conversion factor could be employed to account for such variation. Even so, the ratio of flow comparing two nostrils would likely be valid from measurement to measurement, irrespective of the initial conditions, and therefore still be useful.

Irrespective of the anatomic complexities in the proximal nasal cavity, exhaled nasal airflow can be roughly approximated by a cylindrical tube carrying humidified air of constant temperature 37° C. and relative humidity 100%. According to physical principles, if such airflow emanates directly onto a room temperature glass surface in the setting of an ambient relative humidity <100%, condensation will form on the glass surface. The approximation for nasal airflow is even more precise if two cylinders are used, separated by a small distance Z that considers each nostril as an independent source of airflow (which would only be invalid in cases of septal perforation). Each independent source creates its own plume of condensation that can be measured. Quantifying the amount of water in each plume can be achieved by actual measurement of the condensate. Assuming normal human adult values, tidal volume of air is roughly 490 ml emanating in roughly three (3) seconds of exhalation, with water content of exhaled air being 0.026 g/exhalation.

Therefore, in three (3) seconds of exhalation in the average human adult subject, about 0.026 grams of water are expelled with each tidal exhalation. If the nasal passages are assumed to be equal in cross sectional size, measurement of the water condensed would yield two relatively equal amounts (0.013 cc and 0.013 cc). If the nasal passages, on the other hand, are both significantly obstructed, a smaller amount of water would be measureable in a typical three (3) second standard exhalation. If only one of the two nostrils is significantly obstructed but the other of normal cross sectional area, the condensate measured at the open nostril would approximate the normal value expected, but the condensate as measured from the obstructed nostril would theoretically be only a fraction of normal.

In one embodiment of the present invention, the moisture sensing unit detects the presence of and measures the existence over time of an exhalational plume by means of a moisture sensor (i.e., a device whose physical properties change predictably in the presence of water.) Connecting a voltage source to a flat substrate (such as glass or plastic layered with Indium Nitride (InN), and measuring the change in current across the combined substrate and InN layers in response to the presence of condensation will yield sufficient information to allow a processor to quantitate the individual current densities given by each of the left and right nostril detectors. The resultant current densities are representative of nasal passage airflow, and the given quantities can be used and displayed as needed. It will be understood by those skilled in the art, however, that other types of substrates, as well as compounds with well-understood electrical properties other than InN, could be used to achieve similar functionality.

In another embodiment of the present invention, the moisture sensing unit detects the presence of and measures the existence over time of an exhalational plume by means of a pair of relative humidity sensors (i.e. a device whose physical properties change in relation to atmospheric humidity or water vapor). The humidity sensor output is likewise representative of nasal passage airflow, and the given quantities can be analyzed, used, and displayed as needed. Humidity sensors can be adjusted and tuned to account for variance in background atmospheric humidity. It will be understood by those skilled in the art that several types of commercially-available relative humidity sensors of a desired accuracy could be used in this application.

A third embodiment of the present invention makes use of the measurable optical characteristics of an exhalation plume on a flat surface, such as a glass or mirror. In this embodiment, the condensate plume present on the detector surface registers as a set of measurable pixels on the optical sensor of a camera. The surface area of said plume can be calculated from the pixel values recorded by the camera, and the integral of the full sample of calculated surface areas over time represents the volume density associated with each nostril. Any arrangement of light sources and camera settings, yielding desirable optical properties in terms of image contrast, brightness and focus, suitable for making a precise and analyzable image record of the plume sizes can be used. The moisture plume sample areas could also be subjected to any surface treatment that would optimize their optical performance. It will be understood by those skilled in the art that a wide array of optical sensors, capable of detecting a broad range of wavelengths, could be used in such an application, including camera sensors configured set to record color or monochromatic images.

Embodiments of the present invention can be adapted for use in a variety of clinical or research settings, including, but not limited to, variations that are hand-held, freestanding, flexibly mounted on a cart or wall, or incorporated into an existing item of diagnostic equipment, such as a full nose & mouth mask used in respiratory analysis. Embodiments of the present invention may include an assortment of contoured or adjustable facial contact surfaces, which can aid in orienting the measurement device in relation to the nostrils in a manner that ensures measurement integrity during the procedure while maintaining patient comfort. Embodiments of the present invention may also include a barrier located on the sensing surface at the position of the columellar shadow to reduce the potential for condensation from one plume affecting the surface area readings of the other plume.

Embodiments of the present invention discussed in detail below preferably include an LED display configured to indicate four significant numeric parameters to the user at the conclusion of an exhalation measurement. It will be understood by those skilled in the art that a visual display format other than a numeric layout could also be employed, using any variety of illuminated or mechanical indicators, such as light-emitting diodes, for example, which can convey meaningful information to the user. It will also be understood by those skilled in the art that diagnostically significant information obtained by devices and methods of the present invention would not be limited to the four parameters described below. The processor may be configured to make additional comparisons and calculations as would be desired and other useful parameters associated with various nasal conditions may also be displayed on the LED display. Furthermore, any information resulting from the measurements and calculations undertaken by the present invention can also be saved, transmitted, converted, exported, incorporated into an existing database, or used to drive any external apparatus or process available to the medical or laboratory practitioner.

BRIEF DESCRIPTION OF THE FIGURES

The various advantages of the embodiments of the present invention will become apparent to one skilled in the art by reading the following specification and appended claims, and by referencing the following drawings, in which:

FIG. 2 shows a graph of the relationship between time and the surface area of condensation plumes created by exhalation onto flat glass surfaces.

FIG. 10 depicts the changes over time of the exhalational condensation plumes of two exemplary patients as measured by the present invention.

DETAILED DESCRIPTION OF EXEMPLARY EMBODIMENTS

Non-limiting examples of devices and methods arranged and performed according to certain embodiments of the present invention will now be described in some detail by reference to the accompanying figures.

Figure 1A:
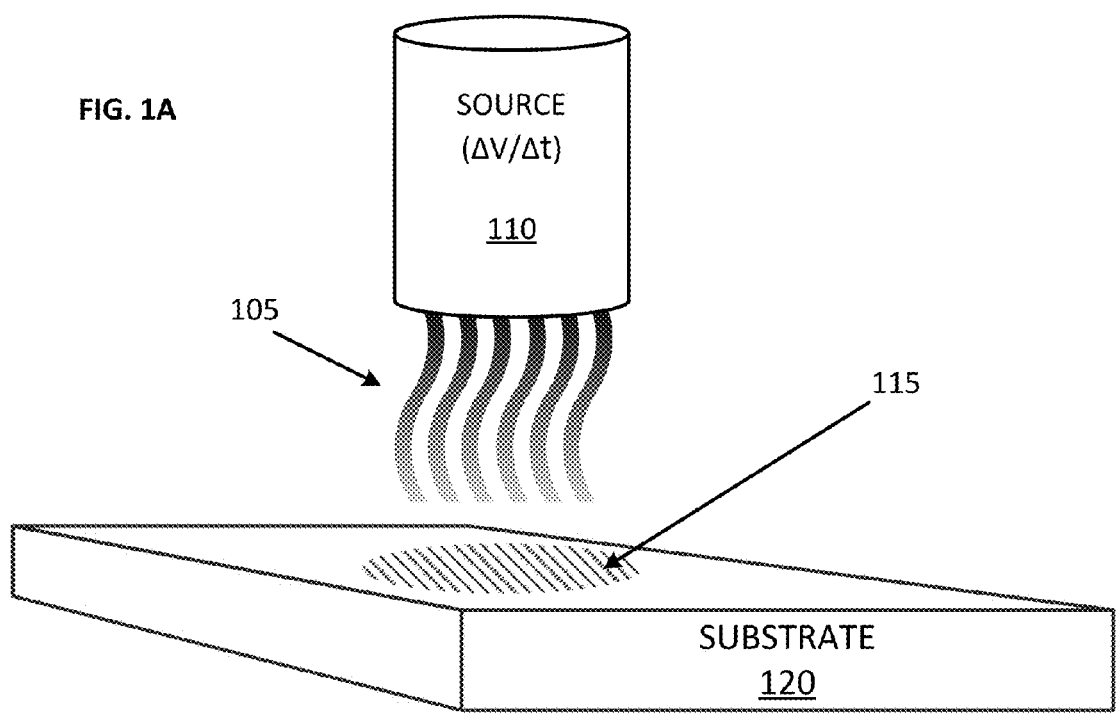
FIGS. 1A and 1B show, respectively, a visible plume of condensation collecting on a substrate in the presence of an air source, such as a human nostril, located directly above the substrate, and the condensation plume patterns forming from two such adjacent airflows separated by distance Z.

FIG. 1A is an orthogonal diagram showing airflow 105 from a source 110 producing a visible plume of condensation 115 on the surface of a substrate 120. The diagonal hatching pattern shown on this and all subsequent figures represents condensation collecting on the surface of a substrate. As discussed above, exhaled nasal airflow 105 can be roughly approximated by a cylindrical tube 110 carrying a flow ($\Delta V/\Delta t$) of humidified air of constant temperature 37° C. and relative humidity 100%. Such airflow produces visible condensation 115 if the airflow is directed to strike a flat surface of a substrate 120 at room temperature. Based on observations of this phenomenon, and using the symbol "$\alpha$" to mean "is directly proportional to," the following five (5) relationships may be observed:
 1) Condensation $\alpha$ $\Delta V/\Delta t$ (Flow) $\alpha$ 1/nasal obstruction
 2) Condensation $\alpha$ Surface Area ($\sigma$) of Plume
 3) Condensation $\alpha$ Length of time for Plume to decay ($\sigma \rightarrow 0$)
 4) Condensation $\alpha$ Amount of Moisture in Gas (assume fixed constant in humans)
 5) Condensation $\alpha$ Temperature Differential between exhaled Gas and Glass/Metal Substrate (at 37 degrees C. and 22 degrees C.).

Given that condensation and condensate surface plumes are both measureable and quantifiable, and with an understanding of the relationships stated above, there is provided in one embodiment of the present invention a method of assessing and diagnosing nasal conditions, such as CNO, by holding a panel of glass (such as a mirror), or plastic, immediately under the nose, orthogonal to the upper lip at the base of the columella, in the same manner as shown by the orientation of substrate 120 to source 110 in FIG. 1A.

Figure 1B:
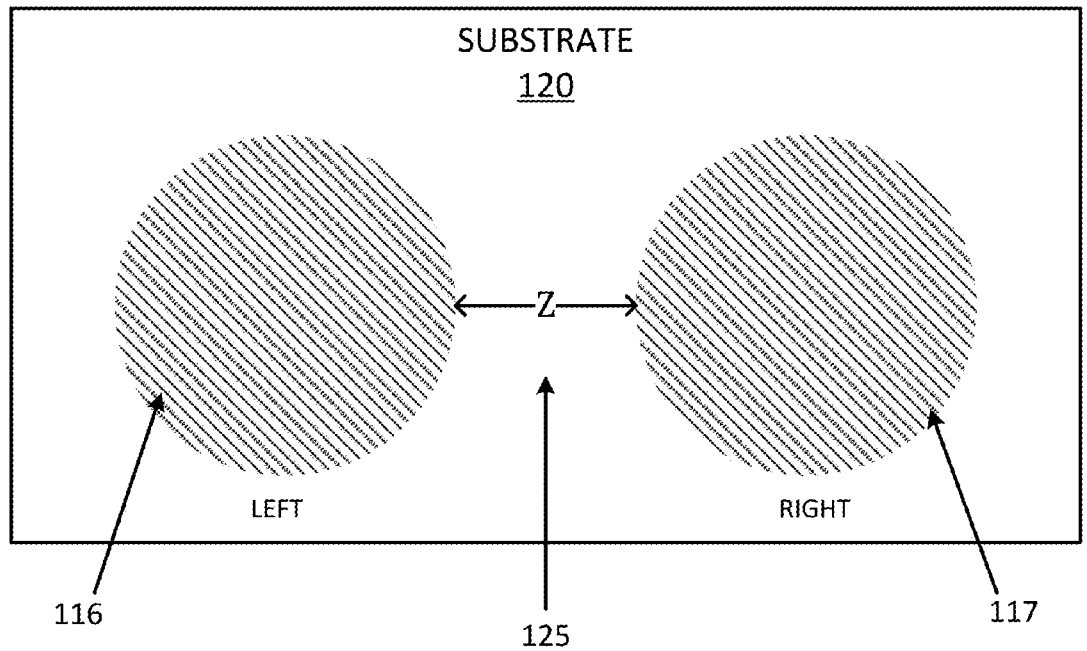

As shown in FIG. 1B, two discrete areas of condensation, corresponding to the left nostril at 116 and the right nostril at 117, are produced following a 3-second tidal exhalation onto substrate 120, which are separated by a distance Z 125 without condensation ("the columellar shadow"). The location of the columellar shadow 125 on the substrate 120 corresponds to the location of the columella between the left and right nostrils. The surface area and density of condensation of each plume on the surface of the glass is directly proportional to the flow through the respective nostrils. In a clinical setting, a medical practitioner can use this observation to assess overall nasal airflow, as well as to judge the difference in airflow between the two nostrils. Consequently, this technique can be utilized in the diagnosis of nasal obstruction, to document patient symptoms, and to assess the response to therapy. It may also be used for patient education, as it provides an immediately apparent visual tool whereby patients can understand the characteristics of their own nasal airflow.

FIG. 2 is a graph representing the relationship between time and the surface area ($\sigma$) of condensation plumes created by exhalation on flat glass surfaces. When exhalation begins at time $t_0$, exhaled air containing moisture begins striking the glass surface, whereupon the moisture condenses to form a plume of condensation on the glass surface. Between time $t_0$ and $t_1$, the volume of exhaled air increases to reach the patient's maximum tidal flow, thereby causing more air and moisture to strike the glass surface between times $t_0$ and $t_1$, which in turn causes the surface area of the condensation plume to propagate in proportion to the volume of air exhaled over time. Between times $t_1$ and $t_2$, the rate of condensation propagating on the surface equals the rate of evaporation of the moisture present, which holds as a steady state until exhalation stops at $t_2$. At this point, only evaporation acts upon the plume of condensation, which decays and ultimately disappears at time $t_3$.

The surface area ($\sigma$) and duration ($t_0$-$t_3$) of condensation associated with each nostril plume is directly proportional to the amount of water that condenses on the glass in response to the flow of air leaving the nasal passage, which in turn is also useful to interpret flow through the respective nostrils. The greater the surface area $\sigma$ and the longer the duration from $t_0$-$t_3$, the greater the amount of condensed water. Since each plume surface area is therefore a function of time, it is represented as $\sigma(t)$. Because the pattern is fully developed at the completion of tidal exhalation, then the area under the curve, or integral of $\sigma(t)$ from the initiation of exhalation ($t_0$) to the complete evaporation of the condensation plume several seconds later ($t_3$) is representative of the total volume of the plume:

$$\text{Plume volume} = \int_{t_0}^{t_3} \sigma(t)$$

Or, in the case of the nose with nostrils A and B, $$\text{Plume volume} = \int_{t_0}^{t_3} \sigma(t) = \int_{t_0}^{t_3} \sigma_A(t) + \int_{t_0}^{t_3} \sigma_B(t)$$

where $\sigma_A(t)$ is the surface area of plume created from nostril A and $\sigma_B(t)$ is the surface area of the plume created from nostril B.

At tidal flows, unforced exhalation correlates closely to inhalation in cases of static (fixed, anatomic) nasal obstruction (e.g. deviated septum or turbinate hypertrophy). Low flow minimizes any Bernoulli effects (narrowing of the nasal valves due to inhalation). In instances of dynamic obstruction (variable, support deficiencies) where obstruction becomes worse with increasing flow, (i.e. nasal valve collapse), the dynamic contribution of obstruction during tidal flow is small so that exhalation measurements still correlate with inhalational flow.

Figure 3:
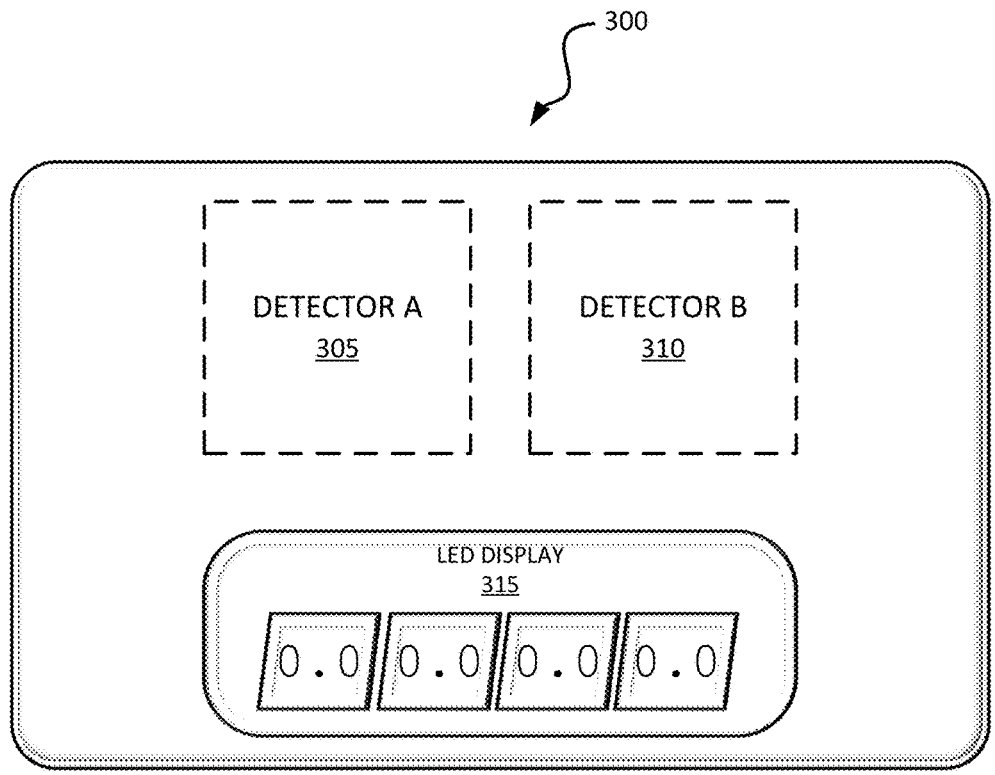
FIG. 3 depicts an exemplary embodiment of a hand-held version of the present invention, including the sensor surfaces and digital display.

FIG. 3 Depicts an exemplary embodiment of the present invention, comprising a handheld device 300 containing a condensate sensor 305 located within the area labeled as Detector A and a twin condensate sensor 310 located within the area labeled as Detector B. Using one of these devices, the current change can be measured in real-time both independently and dependently, in response to exhalational flow from the two nostrils, with the resulting digital output indicated on the device itself via an LED display 315. In some embodiments, the digital display may exhibit four parameters, including without limitation: $\Delta_A$, $\Delta_B$, ($\Delta_A$+$\Delta_B$), as well as ($\Delta_A$/$\Delta_B$), where A and B refer to the twin sensors in the device, and $\Delta_A$, $\Delta_B$ represent changes in electric current in response to condensation arising from nostril A and nostril B, respectively. With these four parameters, clinicians and researchers can assess flow from the nose as a whole, flow from each nostril independently, and as a ratio (with a ratio=1 meaning equal flow in each nostril).

Figure 4:
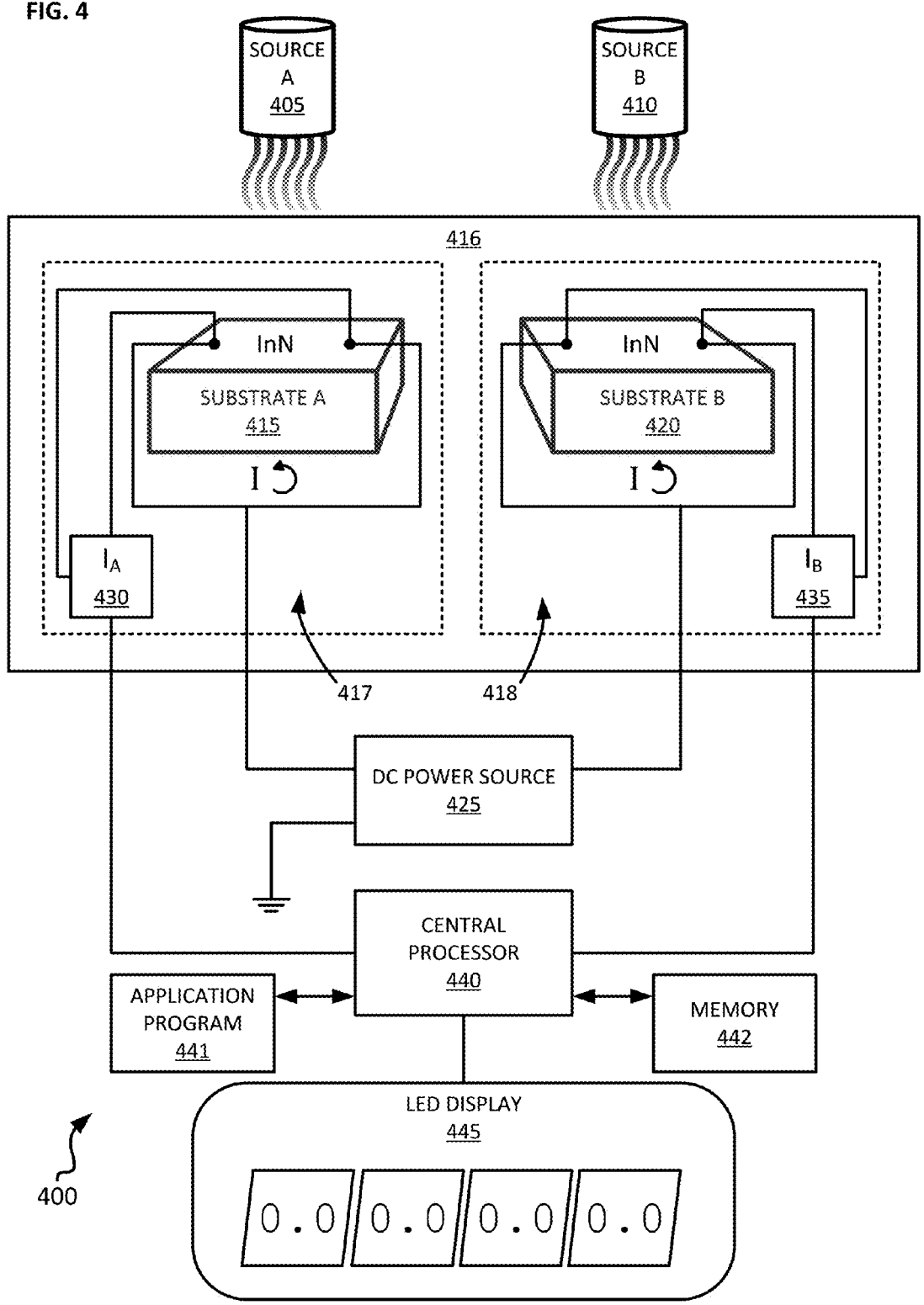
FIG. 4 shows a high-level block diagram illustrating an embodiment of the present invention that utilizes measurements of current change in the moisture sensing unit.

The change in the amount of current flowing across a flat glass surface in response to the presence of condensation on that glass surface has been documented by Dumitru, et al. using indium nitride (InN) condensation sensors (Sensors 2013, 13, 16940-16949). FIG. 4 shows a high-level component diagram of an exemplary embodiment of a device 400 that measures changes in current in response to condensation from nasal exhalation sources A 405 and source B 410 (sources A 405 and B 410 in this figure represent the right and left nostrils of a patient). The handheld device 400 comprises a moisture sensing unit 416 that includes a left nostril detector 417 and a right nostril detector 418, each configured to produce output signals representative of the amounts of moisture currently in contact with said left detector and said right detector. The left nostril detector 417 comprises a layer of indium nitride (InN) deposited on a substrate A 415. The right nostril detector 418 comprises a layer of InN deposited on a substrate B 420. Substrate A 415 and substrate B 420 are connected via parallel circuitry to a switched DC power source 425 and a central processor 440, which has an application program 441 and a memory 442. Current drops across the two detectors 417 and 418 are measured by ammeter 430 and by ammeter 435 in real-time in response to the presence of condensation from nostril exhalation on the sensors. Ammeter 430 and ammeter 435 repeatedly record the current drops across each sensor at fixed 0.001 second intervals from the beginning of exhalation $t=t_0$ until $t=3$ seconds and generate output signals received by processor 440.

In one embodiment of the present invention, the application program 441 causes the processor 440 to perform mathematical operations that inverts the changing current drops as recorded by ammeter 430 and ammeter 435 as a function of time, $I(t)^{-1}$, and integrates it across the duration of the exhalation from $t_0$ to $t_2$, to quantitate the condensation event. The processor 440 calculates the current densities $J_A$, $J_B$ in accordance with the equations given below, and then compares them as a sum $J_A$+$J_B$ and as a quotient $J_A$/$J_B$.

$$\text{Current Density } J_A = \int_{t_0}^{t_2=3} (I_A(t))^{-1}$$

$$\text{Current Density } J_B = \int_{t_0}^{t_2=3} (I_B(t))^{-1}$$

The four resulting parameters, $J_A$, $J_B$, ($J_A$+$J_B$), ($J_A$/$J_B$), are presented on a digital LED display 445. The numbers displayed will remain until the device 400 is reset for a new measurement. Prior to reset, the data can be transmitted via wired or wireless channels (such as USB® or Bluetooth®, for example) to a second device for recording. With these four parameters, clinicians and researchers can assess flow from the nose in total ($J_A$+$J_B$), flow from each nostril independently ($J_A$, $J_B$), and as a ratio ($J_A$/$J_B$) that compares the nostrils to each other, wherein a ratio of $J_A$/$J_B$=1 indicates the flow through nostrils is equal, for example.

Figure 5:
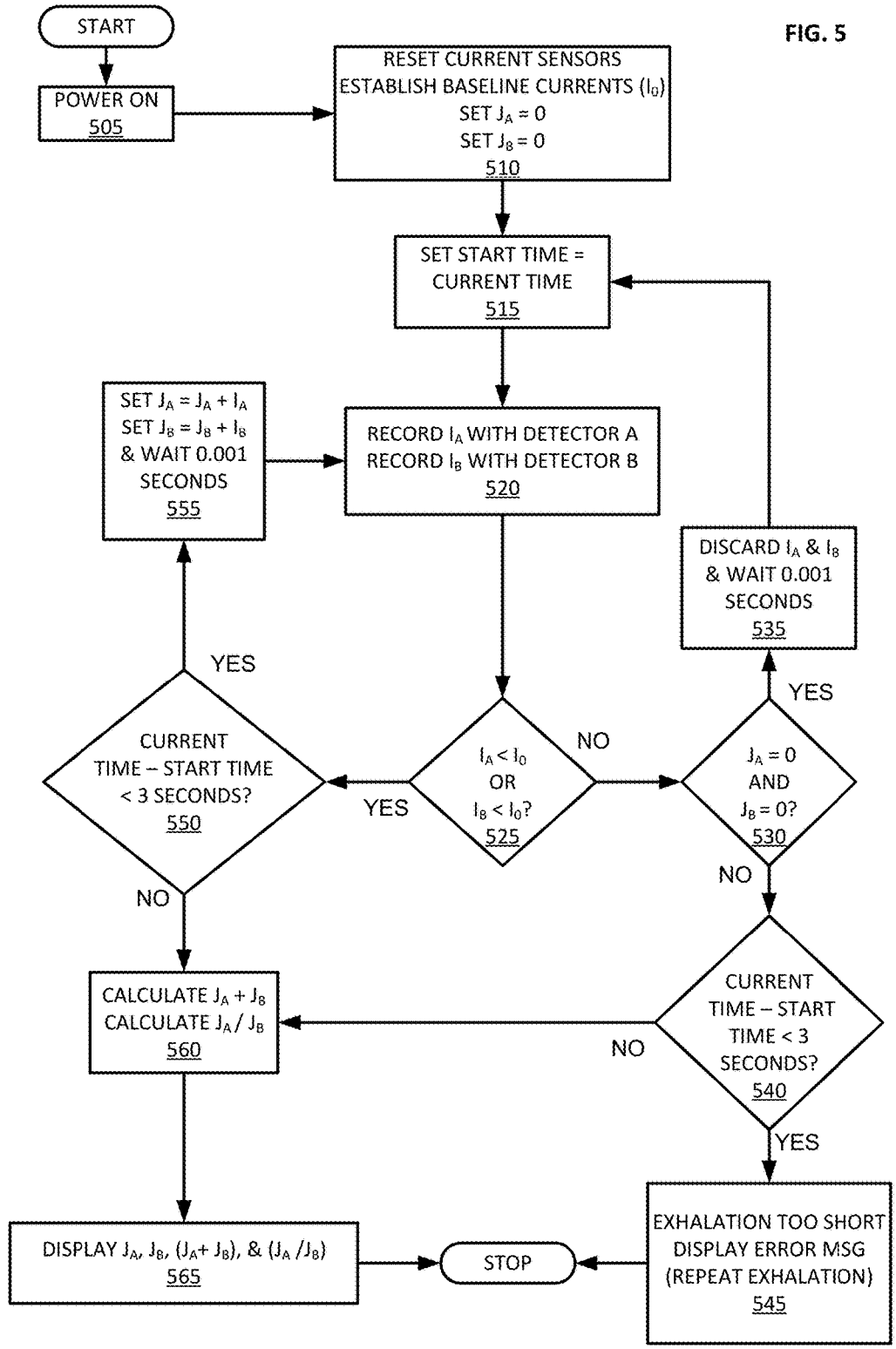
FIG. 5 is a high-level flow diagram illustrating an exemplary algorithm for a process using changes in current density to measure nasal passage airflow as executed by one embodiment of the present invention.

FIG. 5 is a high-level flow diagram illustrating an exemplary algorithm for a process executed by the system of one embodiment of the present invention, such as the device depicted in FIG. 4, in which changes in current density are measured and used to assess nasal passage airflow. The process begins with a power on stage 505 followed by step

510, in which the current sensors are reset, the baseline currents $I_0$ are established, and the variables $J_A$ and $J_B$ are set to take an initial value of zero. Next, at step 515, the start time is set to the current time, and then at step 520 the first current readings are taken by the sensors located at detector A and detector B, yielding the measured currents of $I_A$ and $I_B$. As previously stated, the magnitude of the current flowing across the sensors will drop in the presence of condensation forming on the left and right detectors 417 and 418 of FIG. 4. Therefore, at step 525, the system compares the current values $I_A$ and $I_B$ obtained during step 520 to the baseline current values $I_0$ established at step 510 to determine whether the current flowing across the sensor is greater that the baseline current (no condensation is present). If the value of either $I_A$ or $I_B$ is greater than the baseline current value, the system next checks at step 530 whether the current density variables of $J_A$ and $J_B$ both still hold values of zero. If this is the case, then no airflow has been detected yet. Accordingly, the system loops back to step 535, discards the measured value of $I_A$ and $I_B$, waits for a designated 0.001 seconds, and then resets the start time to the current time to begin another 3 second exhalational measurement.

If the value of either $I_A$ or $I_B$ at step 525 is greater than the baseline current value, and the current density variables of $J_A$ and $J_B$ are not both still at zero, the system moves to check if three (3) seconds has elapsed at step 540; if the measurement interval has been less than three (3) seconds, the system displays an error message at step 545 and the process stops. If three (3) seconds has transpired, then the values of current density variables $J_A$ and $J_B$ are passed on to step 560, in which the sum of the current density variables is taken and the ratio of the current density values is calculated. At this point, the system has determined values for $J_A$, $J_B$, $J_A+J_B$, and $J_A/J_B$, which are then displayed at step 565 before the process halts.

If the value of either $I_A$ or $I_B$ at step 525 is less than the baseline current values $I_0$ established at step 510, then a drop in current has occurred and the system proceeds to step 550 to determine if three (3) seconds have elapsed since the start time in the procedure. As long as the current time minus the start time remains less than three (3) seconds, the system will move on to step 555, during which the value of the current density variables $J_A$ and $J_B$ are added to the measured values of $I_A$ or $I_B$ and the results are stored as the new values for $J_A$ and $J_B$. The system waits for the designated 0.001 seconds and then loops back through steps 520-555. In this manner, a series of successive measurements are taken, and these measurements are quantized and stored until three (3) seconds have elapsed, at which point the system proceeds to step 560 where the system determines values for $J_A$, $J_B$, $(J_A+J_B)$, and $(J_A/J_B)$, which are then displayed at step 565 before the process halts.

In an alternative embodiment, nasal airflow is assessed using the change in relative humidity that occurs as nasal air is exhaled. This embodiment is substantially similar to the device 400 as shown in FIG. 4, except that the left and right nostril detectors comprise twin relative humidity sensors instead of twin layers of InN on substrates. The humidity sensors are each placed at the nasal introitus, just outside the base of each nostril so as not to impair airflow. The device measures the relative humidity at fixed 1/1000th second intervals, similar to the previous embodiment, recording the relative humidity as a function of time RH(t) and integrating it over the same interval $t_0$ to $t_2=3$ seconds, arriving at a quantity RH relative humidity density for each nostril, $RH_A$ and $RH_B$ (units % t).

$$\text{Relative Humidity Density } H_A = \int_{t_0}^{t_2=3} RH_A(t)$$

$$\text{Relative Humidity Density } H_B = \int_{t_0}^{t_2=3} RH_B(t)$$

Figure 6:
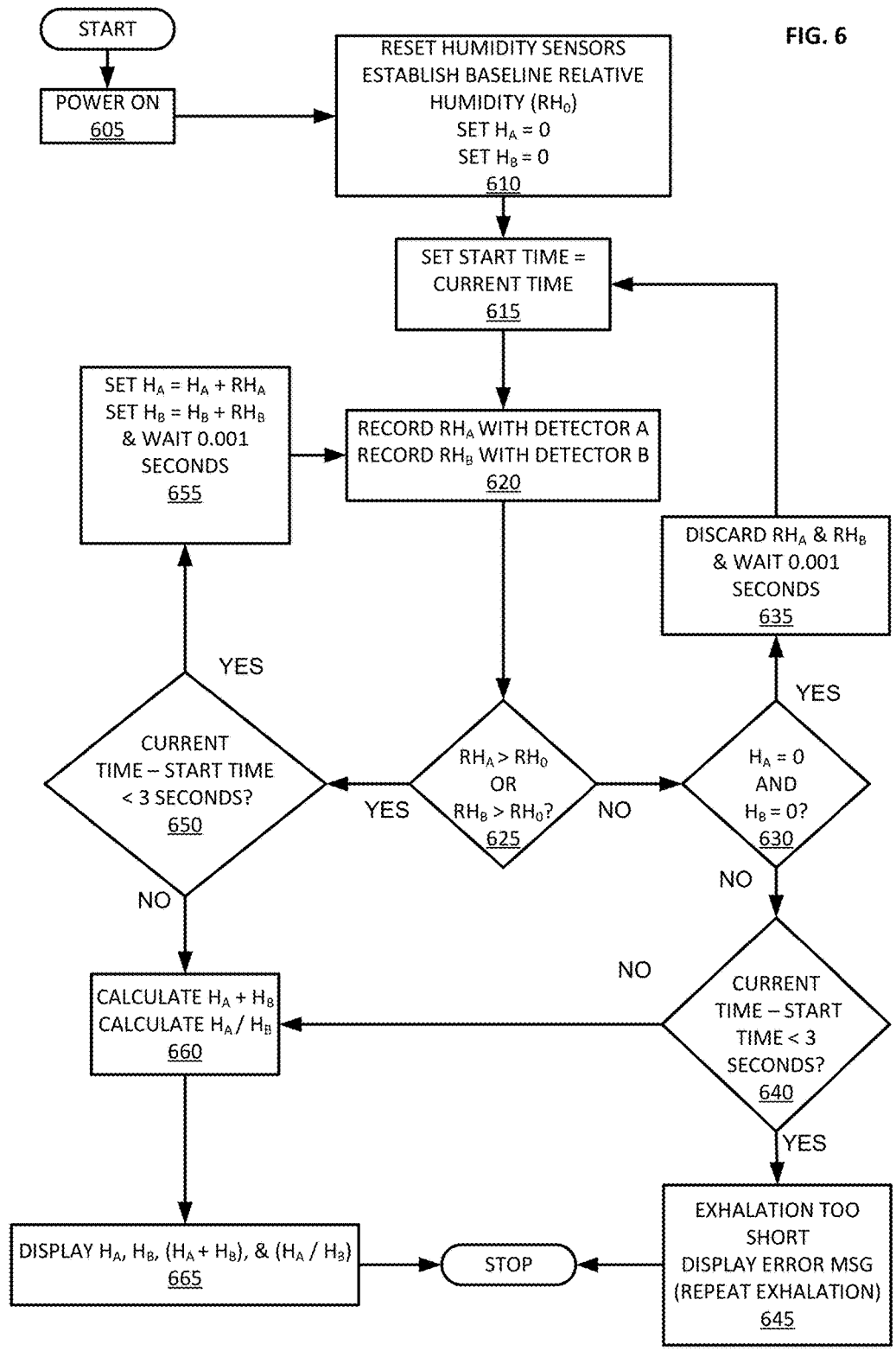
FIG. 6 is a high-level flow diagram illustrating an exemplary algorithm for a process using changes in relative humidity to measure nasal passage airflow as executed by one embodiment of the present invention.

FIG. 6 is a high-level flow diagram illustrating an exemplary algorithm for a process executed by the system of one embodiment of the present invention, which uses changes in relative humidity to assess nasal passage airflow. The process begins with a power on stage 605 followed by step 610, in which the humidity sensors are reset, the baseline relative humidity $RH_0$ is established, and the variables $H_A$ and $H_B$, representing relative humidity density, are set to take an initial value of zero. Next, at step 615, the start time is set as the current time, and then at step 620 the first humidity readings are taken by the sensors located at detector A and detector B, yielding the measured relative humidities of $RH_A$ and $RH_B$. At step 625, the system compares the current values $RH_A$ and $RH_B$ obtained during step 620 with the baseline relative humidity value $RH_0$ established at step 610. If the value of either $RH_A$ or $RH_B$ is not greater than the baseline relative humidity value, the system next checks at step 630 whether the relative humidity density variables of $H_A$ and $H_B$ both still hold values of zero. If this is the case, no airflow has been detected yet. Accordingly, the system loops back to step 635, discards the measured value of $RH_A$ and $RH_B$, waits for a designated 0.001 seconds, and then resets the start time to the current time to begin another three second exhalational measurement.

If the value of either $RH_A$ or $RH_B$ at step 625 is less than the baseline relative humidity value, and the relative humidity density variables of $H_A$ and $H_B$ are not both still at zero, the system next determines whether three (3) seconds have elapsed at step 640. If it has been less than three seconds since the start time, the system displays an error message at step 645 and the process stops. If three seconds have elapsed, then the values of relative humidity density variables $H_A$ and $H_B$ are passed on to step 660, in which a sum of the relative humidity density variables is taken and the ratio of the relative humidity density values is calculated. At this point, the system has determined values for $H_A$, $H_B$, $H_A+H_B$, and $H_A/H_B$, which are then displayed at step 665 before the process halts.

If the value of either $RH_A$ or $RH_B$ at step 625 is greater than the baseline relative humidity value $RH_0$ established at step 610, then the system proceeds to step 650 to determine if three (3) seconds have elapsed since the start time. As long as the current time minus the start time remains less than three (3) seconds, the system will move on to step 655, during which the value of the relative humidity density variables $H_A$ and $H_B$ are added to the measured values of $RH_A$ and $RH_B$ and the results are stored as the new values for $H_A$ and $H_B$. The system waits for the designated 0.001 seconds and then loops back through steps 620-655. In this manner, a series of successive measurements are taken, and these measurements are quantized and stored until the predetermined three (3) second time period has elapsed, at which point the system proceeds to step 660 where the system determines values for $H_A$, $H_B$, $(H_A+H_B)$, and $(H_A/H_B)$, which are then displayed at step 665 before the process halts.

As with the previous embodiment, a digital LED display shows the resulting four parameters: $H_A$, $H_B$, $(H_A+H_B)$, $(H_A/H_B)$. The numbers displayed will remain until the device is reset for a new measurement. Prior to reset, the data can be transmitted via wired or wireless channels (such as USB® or Bluetooth®, for example) to a second device for recording. With these four parameters, clinicians and researchers can assess flow from the nose in total ($H_A+H_B$), flow from each nostril independently ($H_A$, $H_B$), and as a ratio ($H_A/H_B$) that compares the nostrils to each other, with a $H_A/H_B=1$ indicating the flow through nostrils is equal, for example.

Figure 7:
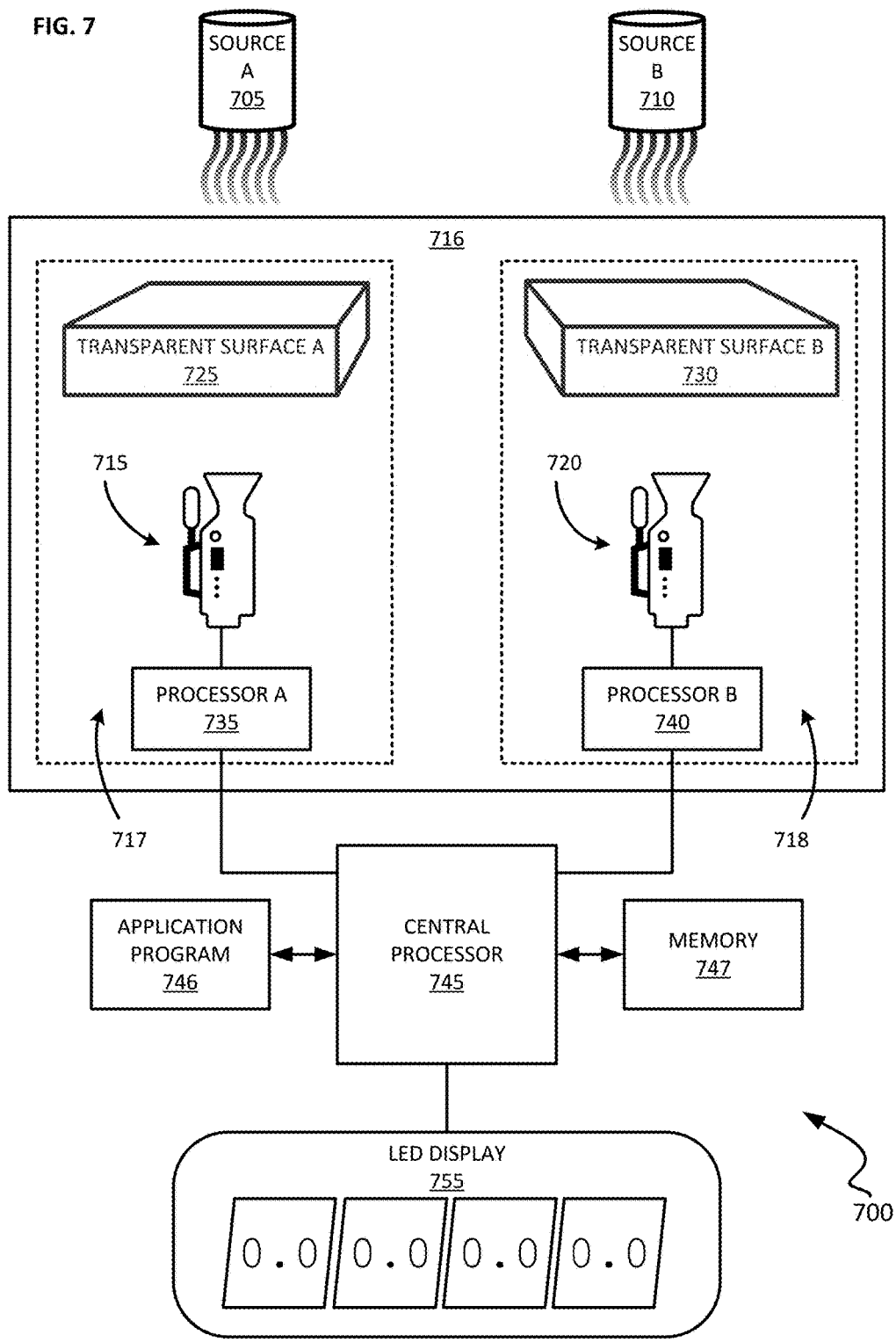
FIG. 7 shows a high-level block diagram illustrating an embodiment of the present invention that utilizes optical measurements of exhalational plume surface areas in the moisture sensing unit.

FIG. 7 shows a high-level component diagram of another exemplary embodiment of a device 700 that measures changes in the surface areas of condensation plumes produced by nasal exhalation source A 705 and source B 710 (sources A 705 and B 710 in this figure represent the right and left nostrils of a patient). In this embodiment, a moisture sensing unit 716 includes a left nostril detector 717 and a right nostril detector 718. The left nostril detector 717 and the right nostril detector 718 comprise twin video cameras 715 and 720, respectively, each with known focal lengths, which are focused on the undersurface of the flat, transparent, surface A 725 and surface B 730, of glass, plastic, or some other optically clear substance. The sources of airflow 705 and 710 are positioned on the opposite side of the optically clear surfaces. Video camera 715 is connected to sub-processor 735, and video camera 720 is connected to sub-processor 740. Sub-processors 735 and 740 are in turn connected to a central processor 745, which has an application program 746 and a memory 747, a switched DC power source 750, and an LED display 755.

The sub-processors 735 and 740 receive images in real time from camera 715 and camera 720, respectively, and the image data is arrayed onto a 1000×1000 pixel grid. If condensation exists within a pixel, that pixel is given a value of 1, and if no condensation exists, then the pixel is given a value of 0. The surface area of each approximately elliptical plume is generated by calculating the number of pixels with value=1 from the center of the grid along orthogonal x- and y-axes to generate radii $r_1$ and $r_2$, and using the relation $\pi r_1 r_2$.

Surface Area Calculation for an Ellipse $$\sigma = \pi r_1 r_2$$

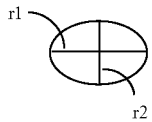

$$\sigma(t) = \pi r_1(t) r_2(t)$$

For example, in a 4×4 cm grid containing 1000×1000 pixels, each pixel is 0.04 mm×0.04 mm.) This measurement is repeated at predetermined regular intervals, such as every 1/1000th second, from the time the condensation first appears ($t_0$) to the time the condensation disappears ($t_3$). In a plume lasting 8 seconds, therefore, each sub-processor would yield 800 values. However, since the time to exhale a tidal volume through a normal (unobstructed) nose can be significantly shorter than an obstructed nose, a more useful measurement is from $t_0$ to $t_2$, which is roughly a 3 second interval in the normal nose. Each of the sub-processors 735 and 740 generates the sum of these surface area values to approximate the integral of $\sigma(t)$ from $t_0$ to $t_2$, where $t_2=3$ seconds.

Nostril A:

$$V_A = \int_{t_0}^{t_2=3} \sigma_A(t)\, dt$$

Nostril B:

$$V_B = \int_{t_0}^{t_2=3} \sigma_B(t)\, dt$$

The output signal of each sub-processor 735 and 740 is labeled $V_A$ and $V_B$, and represents the volume densities associated with nostrils A and B (with units cm2 time). These data $V_A$ and $V_B$ are relayed to a central processor that then calculates the sum ($V_A+V_B$), and the quotient ($V_A/V_B$), representing the total plume condensation volume densities from both nostrils, and the ratio of the plume condensation volume densities, respectively. (A small plume that decays quickly (indicative of minimal condensation and therefore minimal airflow) will yield a small $V_A$ or $V_B$, whereby a large plume that decays slowly (indicative of more condensation and therefore more significant airflow) will yield a large $V_A$ or $V_B$.). While FIG. 7 shows an exemplary embodiment of this device with twin cameras arranged to view the condensation plumes through an optically clear substance, it should be understood that alternate camera and lighting arrangements will also produce analyzable images. For example, cameras set at an angle to a significantly mirrored surface would also be able to record images of the propagation and decay of exhalational condensation plumes.

Figure 8:
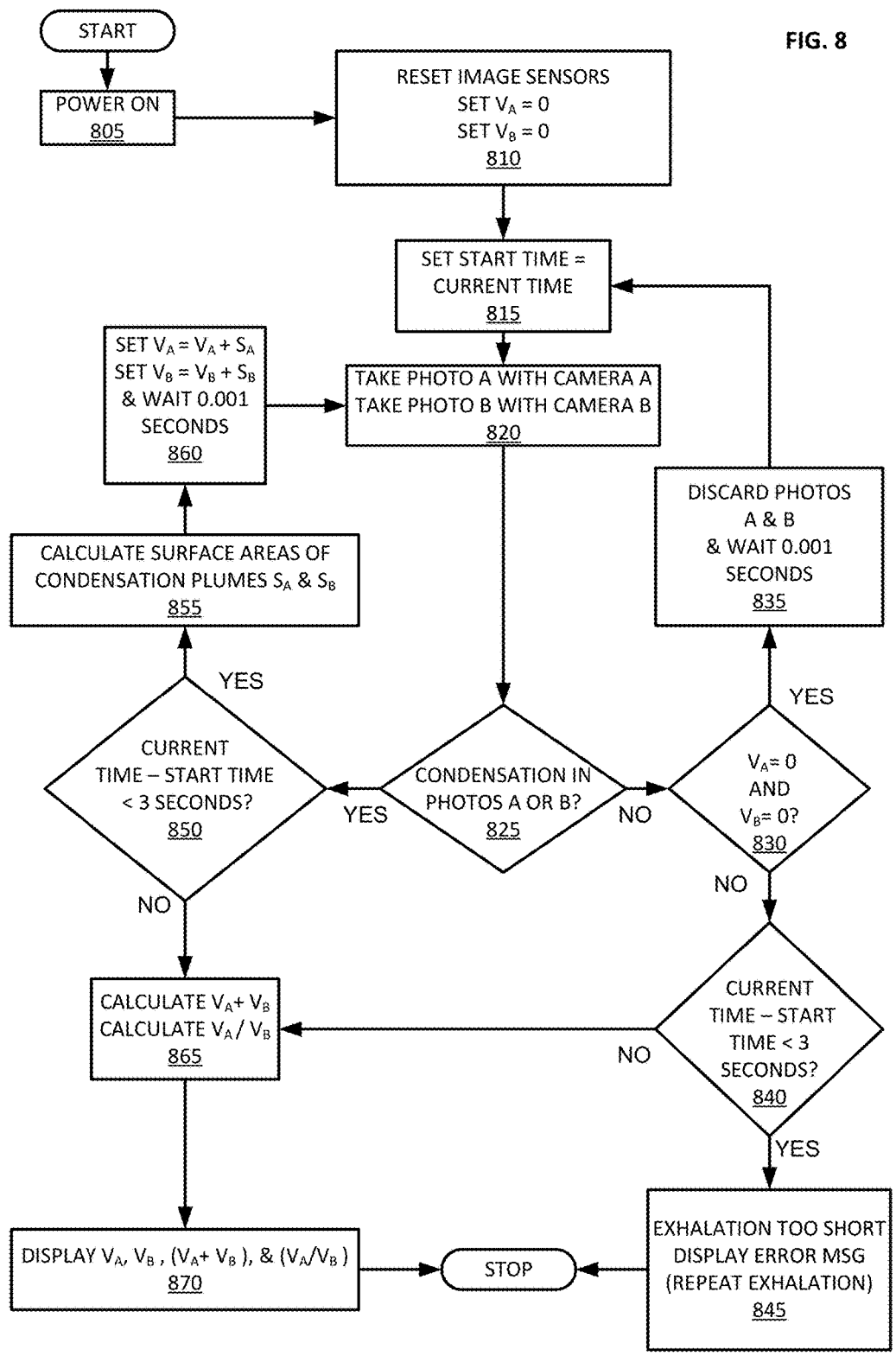
FIG. 8 is a high-level flow diagram illustrating an exemplary algorithm for a process using changes in plume surface area to measure nasal passage airflow as executed by one embodiment of the present invention.

FIG. 8 is a high-level flow diagram illustrating an exemplary algorithm for a process executed by the system of one embodiment of the present invention, which uses information generated from image data to assess nasal passage airflow. The process begins with a power-on stage 805 followed by step 810, in which the image sensors are reset and the variables $V_A$ and $V_B$, representing volume density, are set to take an initial value of zero. Next, at step 815, the start time is set as the current time, and then at step 820 the first images are recorded by the camera A and camera B. The system makes a determination at step 825 as to whether condensation is visible in the images taken by camera A or camera B. If no condensation is present, the system next checks at step 830 whether the volume density variables of $V_A$ and $V_B$ both still hold values of zero. If this is the case, then no airflow has been detected yet and the system loops back to step 835, discards the images taken by camera A and camera B, waits for a designated 0.001 seconds, and then resets the start time to the current time to begin another three (3) second exhalational measurement.

If the system determines at step 825 that condensation is not present in either of the images, and the volume density variables of $V_A$ and $V_B$ both do not hold values of zero, the system checks to see at step 840 if three (3) seconds have elapsed. If the exhalational measurement interval has been less than 3 seconds, the system displays an error message at step 845 and the process stops. If three (3) seconds have elapsed, then the values of volume density variables $V_A$ and $V_B$ are passed on to step 865, in which a sum of the volume density variables is taken and the ratio of the volume density values is calculated. At this point, the system has determined values for $V_A$, $V_B$, $V_A+V_B$, and $V_A/V_B$, which are then displayed at step 870 before the process halts.

If the system determines at step 825 that condensation is indeed present in either image taken by camera A or camera B the system next proceeds to step 850 to determine if three (3) seconds have elapsed in the procedure. As long as the current time minus the start time remains less than 3 seconds, the system will move on to step 855, during which the surface areas of the condensation plumes is calculated in the manner discussed above, and these values are stored as the surface area variables $S_A$ and $S_B$. At step 860, the value of the volume density variables $V_A$ and $V_B$ are added to the calculated surface area values of $S_A$ and $S_B$ and the results are stored as the new values for $V_A$ and $V_B$. The system waits for the designated 0.001 seconds and then loops back through steps 820-860. In this manner, a series of successive image-based measurements are taken, and these measurements are quantized and stored until three (3) seconds have passed, at which point the system proceeds to step 865 where the system determines values for $V_A$, $V_B$, $(V_A+V_B)$, and $(V_A/V_B)$, which are then displayed at step 670 before the process halts.

These four calculated values $V_A$, $V_B$, $(V_A+V_B)$ and $(V_A/V_B)$ are then output to the LED display, such as the one shown as element 755 of device 700, which can be transferred wirelessly to a second device by wired or wireless channel (such as USB® or Bluetooth®) for recording of numerous measurements.

Figure 9:
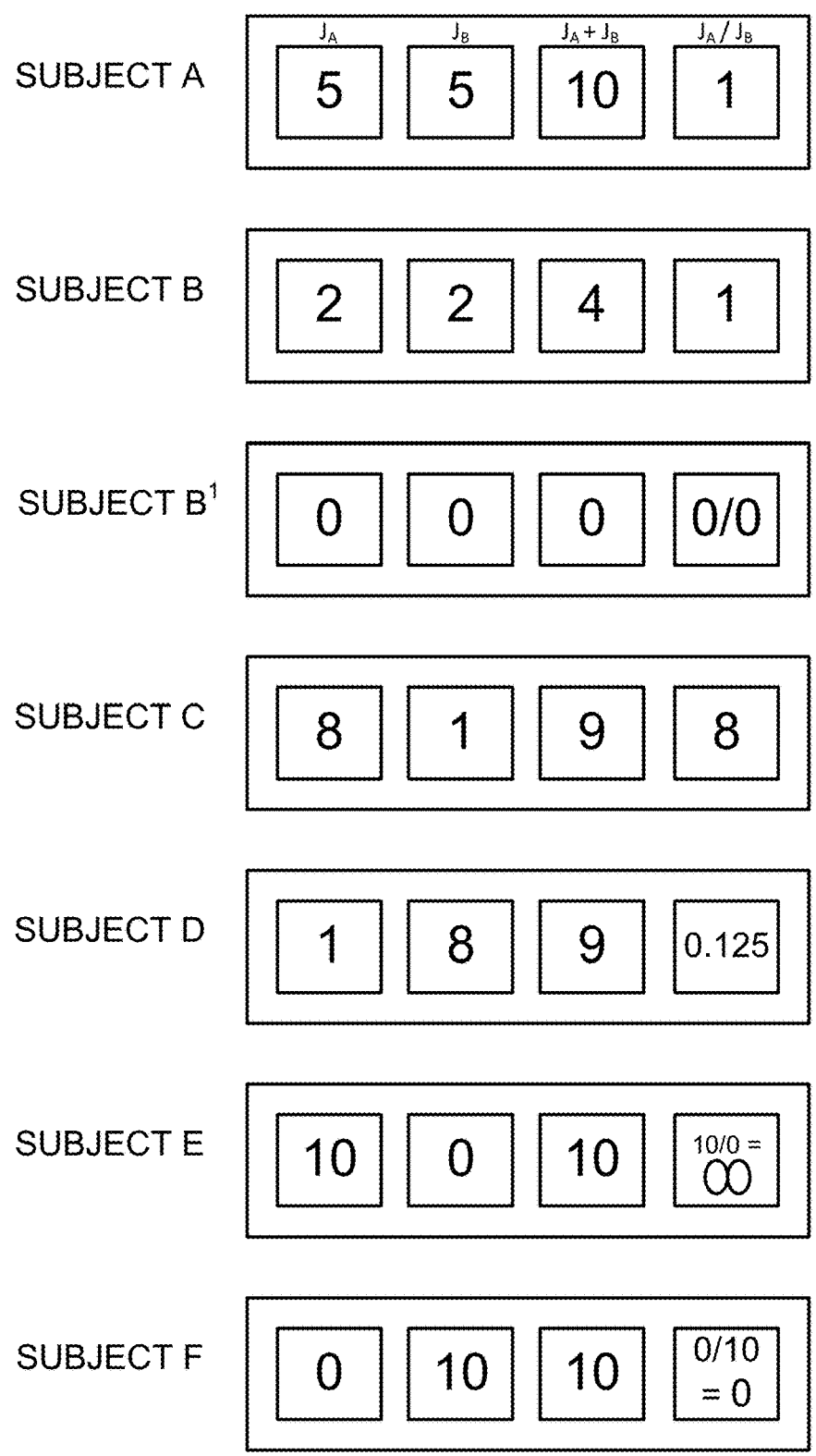
FIG. 9 shows an assortment of possible measurement outcomes as would be visible in a LED display in accordance with embodiments of the present invention.

FIG. 9 shows examples of possible measurement outcomes as would be visible in an LED display in accordance with embodiments of the present invention. The display for Subject A, for instance, shows nasal airflow quantities represented by the current volume density variable $J_A$ and $J_B$ in the first two display positions, and the sum $(J_A+J_B)$ and the ratio $(J_A/J_B)$ of the current density variables in the next two display positions. Viewing these numbers, and assuming the device is configured to use a simple integer range of 1.0 to 10.0, a medical practitioner or researcher can determine that left and right nasal airflow is normal, with $J_A=5$ and $J_B=5$, the overall volume is good $(J_A+J_B=10)$, and a ratio of $(J_A/J_B=1)$ indicating even airflow across both nostrils. The display for Subject B, on the other hand, shows low overall airflow $(J_A+J_B=4)$, but a ratio of $(J_A/J_B=1)$, indicating symmetric restricted airflow. The display for Subject B$^1$, with zeros indicated across the board, clearly shows complete nasal obstruction.

The display for Subject C shows robust flow in the left nostril $(J_A=8)$ and negligible flow in the right nostril $(J_B=1)$; overall nasal airflow is shown as being high $(J_A+J_B=9)$, but given the high ratio $(J_A/J_B=8)$ an incomplete unilateral nasal obstruction of the right nostril is evident. The display for Subject D shows the inverse situation, with negligible flow in the left nostril $(J_A=1)$ and robust flow in the right nostril $(J_B=8)$, which is indicated also by a ratio given as less than zero $(J_A/J_B=0.125)$. In the display for Subject E, high airflow from the left nostril is indicated, along with a complete obstruction of the right nostril. A ratio indicator displaying infinity (or a "division by zero" flag) tells the observer that the right nostril airflow is at absolute zero, indicating a complete unilateral nasal obstruction. In the display for Subject F, high airflow from the right nostril is indicated, along with a complete unilateral obstruction of the left nostril. A ratio indicator showing zero tells the observer that the airflow through the left nostril is completely obstructed.

FIG. 10 depicts the changes over time of the surface area of exhalational condensation plumes of two exemplary patients as would be measured during the predetermined time period by the present invention. The exhalational plumes, which are depicted in FIG. 10 as diagonal hatch patterns, propagate during the interval from $t_0$ to $t_1$, maintain equilibrium between condensation and evaporation during the interval $t_1$ to $t_2$, and then decay during time interval of $t_2$ to $t_3$. The left column, labeled as "SUBJECT A," represents the propagation and decay of twin condensation plumes that correspond to the volume densities indicated on the display for Subject A from FIG. 9. As can be seen, both plumes from each nostril grow to a moderate size prior to decay, and they both grow to an approximately equal surface area. The right column, labeled as "SUBJECT C," represents the propagation and decay of twin condensation plumes that correspond to the volume densities indicated on the display for Subject C from FIG. 9. As can be seen from this series of images, only the left nostril produces a normal plume over the measured predetermined time period, and it is apparent that airflow from the right nostril is substantially impeded. The visible surface areas of the exhalational condensation plumes vary over time and present differently as a result of impediments to nasal airflow. These changes over time, being observable, measureable, and quantifiable, provide the basis for the diagnostic method discussed above.

The above-described preferred embodiments are intended to illustrate the principles of the invention, but not to limit its scope. Various other embodiments, modifications and equivalents to these preferred embodiments may occur to those skilled in the art upon reading the present disclosure or practicing the claimed invention. Such variations, modifications and equivalents are intended to come within the scope of the invention and the appended claims.

What is claimed is:

1. A method of quantifying airflow through a patient's nose using a microprocessor, a memory, an output device and a moisture sensing unit, the moisture sensing unit comprising a left nostril detector and a right nostril detector, each configured to produce output signals representative of the amounts of moisture currently in contact with said left nostril detector and said right nostril detector, respectively, the method comprising the steps of:

a) positioning the moisture sensing unit near the patient's nose while the patient exhales for a predetermined length of time so that a substantial portion of the air expelled from the left nostril of the patient's nose during the exhalation will strike the left nostril detector and a substantial portion of the air expelled from the right nostril of the patient's nose during the exhalation will strike the right nostril detector;

b) during the predetermined length of time, repetitively recording the output signals produced by the left nostril detector of the moisture sensing unit, thereby generating a plurality of discrete output signals for the left nostril, the plurality of discrete output signals representing the changes in output signals produced by the left nostril detector in response to changes in the amount of moisture in contact with the left nostril detector, and storing the plurality of discrete output signals for the left nostril in the memory;

c) during the predetermined length of time, repetitively recording the output signals produced by the right nostril detector of the moisture sensing unit, thereby generating a plurality of discrete output signals for the right nostril, the plurality of discrete output signals representing the changes in output signals produced by the right nostril detector in response to changes in the amount of moisture in contact with the right detector, and storing the plurality of discrete output signals for the right nostril in the memory;

d) with the microprocessor, calculating a left nostril flow density by summing the discrete output signals in the plurality of discrete output signals for the left nostril, and calculating a right nostril flow density by summing the discrete output signals in the plurality of discrete output signals for the right nostril;

e) presenting the left nostril flow density and the right nostril flow density on the output device;

f) wherein the left nostril detector and the right nostril detector of the moisture sensing unit each comprises either:

f1) a low conductivity substrate with a flat surface; a layer of a high conductivity material affixed to the flat surface of the low conductivity substrate; a power source configured to pass an electric current through the layer of high conductivity material; an ammeter configured to produce an output signal; wherein (i) at least some of the moisture in the air expelled from the patient's nostril condenses on the layer of high conductivity material, (ii) the magnitude of electric current passing through the layer of high conductivity material varies in response to changes in the amount of condensed moisture in contact with the layer of high conductivity material, and (iii) the output signal produced by the ammeter varies in direct proportion to changes in the magnitude of the electric current passing through the layer of high conductivity material; or f2) a transparent material with a flat surface; a video camera having a lens that is focused on the flat surface of the transparent material; and a sub-processor configured to receive image data from the video camera during the exhalation of the patient onto the moisture sensing unit and to calculate, based on the received image data, the surface area of a plume of condensed moisture collected on the flat surface of the transparent material during the exhalation, and to produce the output signal that varies in direct proportion to changes in the surface area of the plume of condensed moisture collected on the flat surface of the transparent material; or f3) a humidity sensor; a sub-processor configured to (i) receive humidity data from the humidity sensor during the exhalation of the patient onto the moisture sensing unit, (ii) to calculate, based on the received humidity data, the relative humidity of the air expelled from the patient's nostril during the exhalation, and (iii) to produce an output signal that varies in direct proportion to changes in the relative humidity of the air expelled from the patient's nostril.

2. The method of claim 1, further comprising:
a) calculating with the microprocessor a sum of the left nostril flow density and the right nostril flow density; and
b) presenting the sum on the output device.

3. The method of claim 1, further comprising:
a) calculating with the microprocessor a ratio of the left nostril flow density to the right nostril flow density; and
b) presenting the ratio on the output device.

4. The method of claim 1, wherein the output device comprises a digital display screen.

5. The method of claim 1, wherein:
a) the output device comprises one or more light emitting diodes; and b) presenting the left nostril flow density and the right nostril flow density on the output device comprises activating the one or more light emitting diodes.

6. The method of claim 1, wherein the predetermined length of time is between three and five seconds.

7. The method of claim 1, wherein the predetermined length of time is about three seconds.

8. The method of claim 1, wherein the low conductivity substrate comprises a piece of glass or a piece of plastic.

9. The method of claim 1, wherein the high conductivity material comprises indium nitride (InN).

10. A nasal airflow evaluation instrument, comprising:
a) a microprocessor;
b) a memory;
c) an output device;
d) a moisture sensing unit comprising a left nostril detector and a right nostril detector, the left nostril detector and the right nostril detector each configured to produce output signals representative of the amounts of moisture currently in contact with said left nostril detector and said right nostril detector, respectively; and
e) an application program stored in the memory, the application program comprising program instructions that, when executed by the microprocessor, will cause the microprocessor to
(i) activate the moisture sensing unit;
(ii) repetitively record the output signals produced by the left nostril detector of the moisture sensing unit over a predetermined length of time, thereby generating a plurality of discrete output signals for the left nostril, the plurality of discrete output signals representing the changes in output signals produced by the left nostril detector in response to changes in the amount of moisture in contact with the left nostril detector, and store the plurality of discrete output signals for the left nostril in the memory,
(iii) repetitively record the output signals produced by the right nostril detector of the moisture sensing unit over a predetermined length of time, thereby generating a plurality of discrete output signals for the right nostril, the plurality of discrete output signals representing the changes in output signals produced by the right nostril detector in response to changes in the amount of moisture in contact with the right nostril detector, and store the plurality of discrete output signals for the right nostril in the memory,
(iv) calculate a left nostril flow density by adding together the discrete output signals in the plurality of discrete output signals for the left nostril,
(v) calculate a right nostril flow density by adding together the discrete output signals in the plurality of discrete output signals for the right nostril, and
(vi) present the left nostril flow density and the right nostril flow density on the output device,
f) wherein the left nostril detector and the right nostril detector of the moisture sensing unit each comprises either:
f1) a low conductivity substrate with a flat surface; a layer of a high conductivity material affixed to the flat surface of the low conductivity substrate; a power source configured to pass an electric current through the layer of high conductivity material; an ammeter configured to produce an output signal; wherein (i) at least some of the moisture in the air expelled from the patient's nostril condenses on the layer of high conductivity material, (ii) the magnitude of electric current passing through the layer of high conductivity material varies in response to changes in the amount of condensed moisture in contact with the layer of high conductivity material, and (iii) the output signal produced by the ammeter varies in direct proportion to changes in the magnitude of the electric current passing through the layer of high conductivity material; or f2) a transparent material with a flat surface; a video camera having a lens that is focused on the flat surface of the transparent material; and a sub-processor configured to receive image data from the video camera during the exhalation of the patient onto the moisture sensing unit and to calculate, based on the received image data, the surface area of a plume of condensed moisture collected on the flat surface of the transparent material during the exhalation, and to produce the output signal that varies in direct proportion to changes in the surface area of the plume of condensed moisture collected on the flat surface of the transparent material; or f3) a humidity sensor; a sub-processor configured to (i) receive humidity data from the humidity sensor during the exhalation of the patient onto the moisture sensing unit, (ii) to calculate, based on the received humidity data, the relative humidity of the air expelled from the patient's nostril during the exhalation, and (iii) to produce an output signal that varies in direct proportion to changes in the relative humidity of the air expelled from the patient's nostril.

11. The nasal airflow evaluation instrument of claim 10, wherein the application program further includes program instructions that, when executed by the microprocessor, will cause the microprocessor to:
a) calculate a sum of the left nostril flow density and the right nostril flow density; and
b) present the sum on the output device.

12. The nasal airflow evaluation instrument of claim 10, wherein the application program further includes program instructions that, when executed by the microprocessor, will cause the microprocessor to:
a) calculate a ratio of the left nostril flow density to the right nostril flow density; and
b) present the ratio on the output device.

13. The nasal airflow evaluation instrument of claim 10, wherein the output device comprises a digital display screen.

14. The nasal airflow evaluation instrument of claim 10, wherein:
a) the output device comprises one or more light emitting diodes; and
b) the application program further includes program instructions that, when executed by the microprocessor, will cause the microprocessor to activate the one or more light emitting diodes.

15. The nasal airflow evaluation instrument of claim 10, wherein the predetermined length of time is between two and five seconds.

16. The nasal airflow evaluation instrument of claim 10, wherein the predetermined length of time is about three seconds.

17. The nasal airflow evaluation instrument of claim 10, wherein the low conductivity substrate comprises a piece of glass or a piece of plastic.

18. The nasal airflow evaluation instrument of claim 10, wherein the high conductivity material comprises indium nitride (InN).

19. The nasal airflow evaluation instrument of claim 10, wherein the moisture sensing unit further comprises a partition, interposed between the left nostril detector and the right nostril detector, the partition being configured to reduce cross-mixing of air expelled from the patient's left and right nostrils, respectively, prior to said air striking the left nostril detector and the right nostril detector.

* * * * *